(12) United States Patent
Sierro

(10) Patent No.: US 9,267,871 B2
(45) Date of Patent: Feb. 23, 2016

(54) RHEOMETER OR VISCOMETER

(75) Inventor: Philippe Sierro, Haguenau (FR)

(73) Assignee: Thermo Electron (Karlsruhe) GmbH, Karlsruhe (DE)

( * ) Notice: Subject to any disclaimer, the term of this patent is extended or adjusted under 35 U.S.C. 154(b) by 624 days.

(21) Appl. No.: 13/293,408

(22) Filed: Nov. 10, 2011

(65) Prior Publication Data

US 2012/0111097 A1    May 10, 2012

(30) Foreign Application Priority Data

Nov. 10, 2010    (DE) .................... 10 2010 050 973

(51) Int. Cl.
*G01N 11/14*    (2006.01)
*G01N 11/16*    (2006.01)

(52) U.S. Cl.
CPC ............ *G01N 11/142* (2013.01); *G01N 11/165* (2013.01)

(58) Field of Classification Search
CPC ... G01N 11/16; G01N 11/165; G01N 11/142; G01N 2011/145
USPC ........................................................ 73/54.41
See application file for complete search history.

(56) References Cited

U.S. PATENT DOCUMENTS

| | | | |
|---|---|---|---|
| 3,667,286 A * | 6/1972 | Kaufman et al. ............. | 73/54.29 |
| 4,002,960 A | 1/1977 | Brookfield et al. | |
| 4,202,204 A * | 5/1980 | Hartert .......................... | 73/64.42 |
| 4,425,986 A | 1/1984 | Wedlin | |
| 4,435,080 A * | 3/1984 | Maly et al. .................... | 356/426 |
| 4,611,487 A | 9/1986 | Krenn et al. | |
| 4,643,020 A * | 2/1987 | Heinz .......................... | 73/54.27 |
| 4,678,978 A | 7/1987 | Curtis | |
| 4,877,999 A | 10/1989 | Knapp et al. | |
| 5,095,278 A | 3/1992 | Hendrick | |
| 5,165,792 A | 11/1992 | Crowe et al. | |
| 5,167,143 A | 12/1992 | Brookfield | |
| 5,201,214 A | 4/1993 | Sekiguchi et al. | |
| 5,287,732 A | 2/1994 | Sekiguchi | |
| 5,368,391 A | 11/1994 | Crowe et al. | |
| 5,484,204 A | 1/1996 | Damley | |

(Continued)

FOREIGN PATENT DOCUMENTS

| DE | 10047793 B4 | 9/2005 |
|---|---|---|
| DE | 102004050751 | 4/2006 |

(Continued)

OTHER PUBLICATIONS

Thermo Scientific HAAKE RheoStress 6000, Modulares Universal-Rheometer, brochure, 16 pages, 2011.

(Continued)

*Primary Examiner* — Laura Martin
*Assistant Examiner* — Alex Devito
(74) *Attorney, Agent, or Firm* — Gordon Stewart

(57) ABSTRACT

A rheometer or viscometer has a first measuring part and a second measuring part, between which a sample space for receiving a material sample is formed. By means of a drive device, at least the second measuring part can be rotated and/or can be oscillated, it being possible for the drive movement of the drive device to be transferred to the second measuring device via a transmission element. The drive device is arranged on the side of the first measuring part that is facing away from the second measuring part and the transmission element penetrates through the first measuring part, particularly at a through-bore.

11 Claims, 2 Drawing Sheets

(56) References Cited

U.S. PATENT DOCUMENTS

Figure 1:
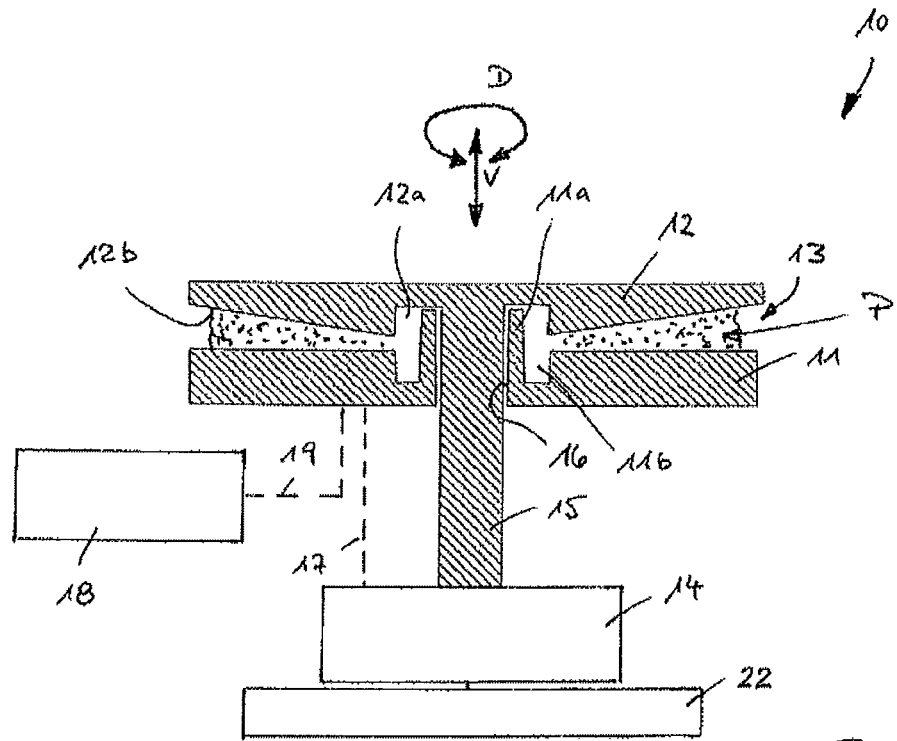

| | | | |
|---|---|---|---|
| 5,503,003 A | 4/1996 | Brookfield | |
| 5,531,102 A | 7/1996 | Brookfield et al. | |
| 5,535,619 A | 7/1996 | Brookfield | |
| 5,540,088 A | 7/1996 | Hall | |
| 5,601,745 A | 2/1997 | Schalk et al. | |
| 5,637,803 A | 6/1997 | Schalk et al. | |
| 5,777,212 A | 7/1998 | Sekiguchi et al. | |
| 5,821,407 A | 10/1998 | Sekiguchi et al. | |
| 5,874,665 A | 2/1999 | Larsson | |
| 5,874,666 A | 2/1999 | Bishop | |
| 5,886,268 A | 3/1999 | Larsson | |
| 5,915,283 A | 6/1999 | Reed et al. | |
| 5,922,609 A | 7/1999 | Kellner et al. | |
| 5,973,299 A | 10/1999 | Reader, Jr. | |
| 6,167,752 B1 | 1/2001 | Raffer | |
| 6,200,022 B1 | 3/2001 | Hammiche et al. | |
| 6,240,770 B1 | 6/2001 | Raffer | |
| 6,499,336 B1 | 12/2002 | Raffer | |
| 6,539,779 B2 | 4/2003 | Brookfield | |
| 6,571,610 B1 | 6/2003 | Raffer | |
| 6,588,254 B1 | 7/2003 | Foster et al. | |
| 6,644,136 B1 | 11/2003 | Carney et al. | |
| 6,652,015 B1 | 11/2003 | Carney et al. | |
| 6,698,275 B2 | 3/2004 | Hall | |
| 6,714,879 B2 | 3/2004 | Evans et al. | |
| 6,798,099 B1 | 9/2004 | Doe | |
| 6,823,278 B1 | 11/2004 | Carney et al. | |
| 6,846,455 B1 | 1/2005 | Carney et al. | |
| 6,859,271 B1 | 2/2005 | Carney et al. | |
| 6,874,351 B2 | 4/2005 | Bloder et al. | |
| 6,931,915 B2 | 8/2005 | Garritano et al. | |
| 6,971,262 B1 | 12/2005 | Marchal et al. | |
| 7,017,393 B2 | 3/2006 | Doe et al. | |
| 7,096,728 B2 | 8/2006 | Garritano et al. | |
| 7,135,874 B2 | 11/2006 | Berting et al. | |
| 7,137,290 B2 | 11/2006 | Doe et al. | |
| 7,168,299 B2 | 1/2007 | Doe et al. | |
| 7,189,441 B2 | 3/2007 | Denis et al. | |
| 7,207,210 B2 | 4/2007 | Moonay | |
| 7,247,698 B2 | 7/2007 | Denis et al. | |
| 7,275,419 B2 | 10/2007 | Raffer | |
| D565,331 S | 4/2008 | Miller | |
| 7,367,224 B2 | 5/2008 | Platzek et al. | |
| 7,500,385 B2 | 3/2009 | Liberatore et al. | |
| 7,526,941 B2 | 5/2009 | Doe | |
| 7,594,429 B2 | 9/2009 | Liberatore et al. | |
| 7,607,098 B2 | 10/2009 | Grehlinger et al. | |
| 2008/0022758 A1* | 1/2008 | Cottais et al. | 73/54.32 |

FOREIGN PATENT DOCUMENTS

| | | |
|---|---|---|
| DE | 10206710 B4 | 4/2007 |
| DE | 19708323 B4 | 7/2007 |
| WO | 2003048743 A1 | 6/2003 |

OTHER PUBLICATIONS

Modular Rheometer Platform for Individual Demands, Thermo Scientific HAAKE MARS III, brochure, 28 pages, 2009.

* cited by examiner

RHEOMETER OR VISCOMETER

Embodiments of the invention relates to a rheometer or viscometer with a first measuring part and a second measuring part, between which a sample space for receiving a material sample is formed, and with a drive device, by means of which at least the second measuring part can be rotated and/or can be oscillated, it being possible for the drive movement of the drive device to be transferred to the second measuring device via a transmission element. Embodiments of the invention are described below, it being understood that the invention is not limited to the described embodiments and many variations and other embodiments of the invention are possible. When reference is made to a "preferred" feature, it will be understood that this in no way intended to limit the scope of the present invention. What is preferred in one situation may not be preferred in another.

A rheometer is a measuring instrument for determining the deformation and flow behavior of a substance. A viscometer serves for determining the viscosity of a liquid. Both types of instrument are expressly intended to be covered by the present invention, but a rheometer is taken as a basis hereafter by way of example.

The measuring of rheological variables in a rheometer is based on the exact knowledge of the relationship between the shear stress and the deformation of a material sample. To be able to derive the material properties, for example the viscosity or the modulus of elasticity, from these variables, the shear stress and the deformation of the material sample must be determined as accurately as possible. For this purpose, it is usual to introduce the material sample into a sample space which is formed between two measuring parts, for example in the form of plates. However, other geometries of the measuring parts, for example a conical, cylindrical, cup-shaped or blade-shaped geometry, are also known and are expressly intended to be covered by the present invention.

Usually, the two measuring parts are arranged one above the other, which is to be assumed hereafter by way of example. However, the invention is also not restricted to this, but instead the measuring parts may also be arranged next to one another or obliquely. It is intended to be assumed hereafter that a first, lower measuring part and a second, upper measuring part are provided, between which the sample space for receiving the material sample is formed.

The first, lower measuring part is usually of a fixed form (that is, not rotatable or adjustable), and arranged at a distance above the first measuring part is the second, upper measuring part, which can be rotated and/or can be oscillated. In addition, the distance between the measuring parts can be changed by adjusting the second, upper measuring part. To introduce the material sample into the sample space, it is additionally known to move the second, upper measuring part up by a relatively great amount or to move it away from the first measuring part, in order that the user has sufficient room to place the material sample in the sample space.

Provided as the drive for the movement of the second, upper measuring part is a drive device in the form of an electric motor, particularly a servomotor, which is arranged above the second, upper measuring part and the rotational movement of which is transferred to the second, upper measuring part via a transmission element in the form of a vertical shaft. Since the distance of the drive device from the sample space must be sufficiently great to be able to raise the second, upper measuring part by a sufficient amount to fill the sample space, a rheometer requires a relatively great installation space, particularly above the sample space, which is disadvantageous.

Embodiments of the invention can provide a rheometer or viscometer of the type mentioned which has a compact construction and, as a result, is handy.

It is thereby provided that the drive device driving the second, upper measuring part is arranged on a side of the first measuring part that is facing away from the second measuring part and that the transmission element penetrates through the first measuring part.

The drive device, which in the usual way may be an electric motor and particularly a servomotor, is not arranged together with the second, upper measuring part on the same side of the first, lower measuring part—as otherwise usual—but instead is seated on the side of the first, lower measuring part that is facing away from the second, upper measuring part, i.e. under it. The transmission element, which is preferably a shaft, penetrates through the first, lower measuring part, so that the drive movement of the drive device lying under the first, lower measuring part can be transferred through the first, lower measuring part to the second, upper measuring part lying thereabove.

In this way, the installation space above the second, upper measuring part can be left free, so that the rheometer is of a much smaller and more compact form.

In a preferred design of the invention, it is provided that in the first measuring part there is formed a through-bore, through which the transmission element is led, preferably with a close fit. The first, lower measuring part may in this case serve at the same time for the rotatable mounting of the transmission element, and particularly the corresponding shaft.

A seal may be arranged between the transmission element or the shaft and the first, lower measuring part, in order to prevent part of the material sample from penetrating into the through-bore. In a preferred design of the invention, however, it is provided that the transmission element or the shaft penetrates through the through-bore without a seal. In the case without a seal, the "close" fit may be such as to prevent sample from penetrating into the through-bore to any extent which will inhibit the instrument performance (ideally with no such penetration).

The first, lower measuring part is preferably likewise of a fixed, i.e. rotationally fixed, form, but it may alternatively also be provided that the first, lower measuring part is likewise able to rotate and/or able to oscillate. In this case, the first, lower measuring part may be provided with a drive device of its own, but in a preferred design of the invention it is provided that the drive movement for the first, lower measuring part is also derived from the drive device of the second, upper measuring part, i.e. that the first, lower measuring part and the second, upper measuring part are driven by means of a common drive device.

Figure 2:
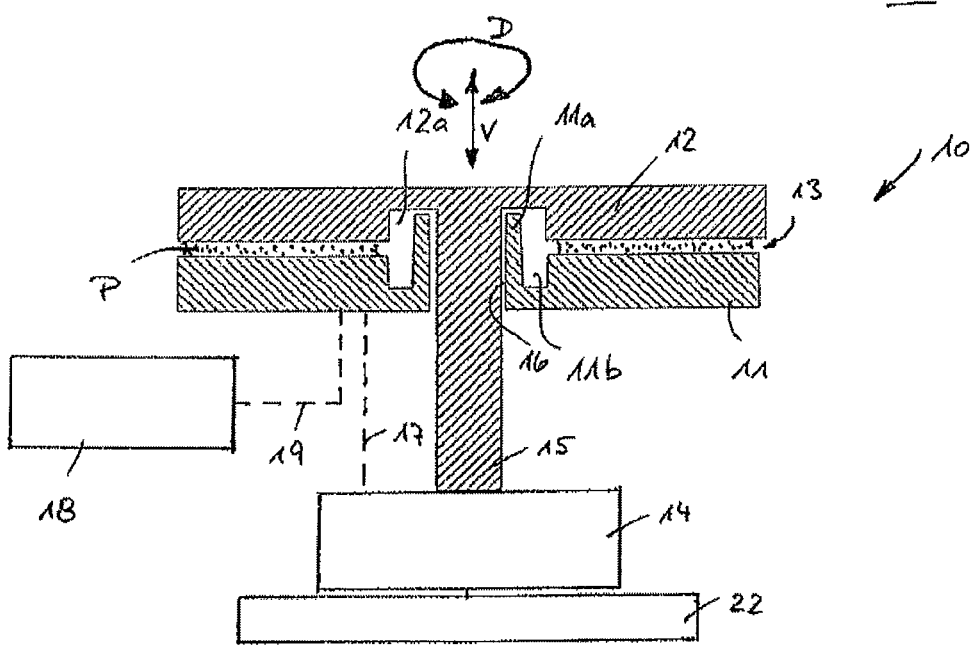
Figure 3:
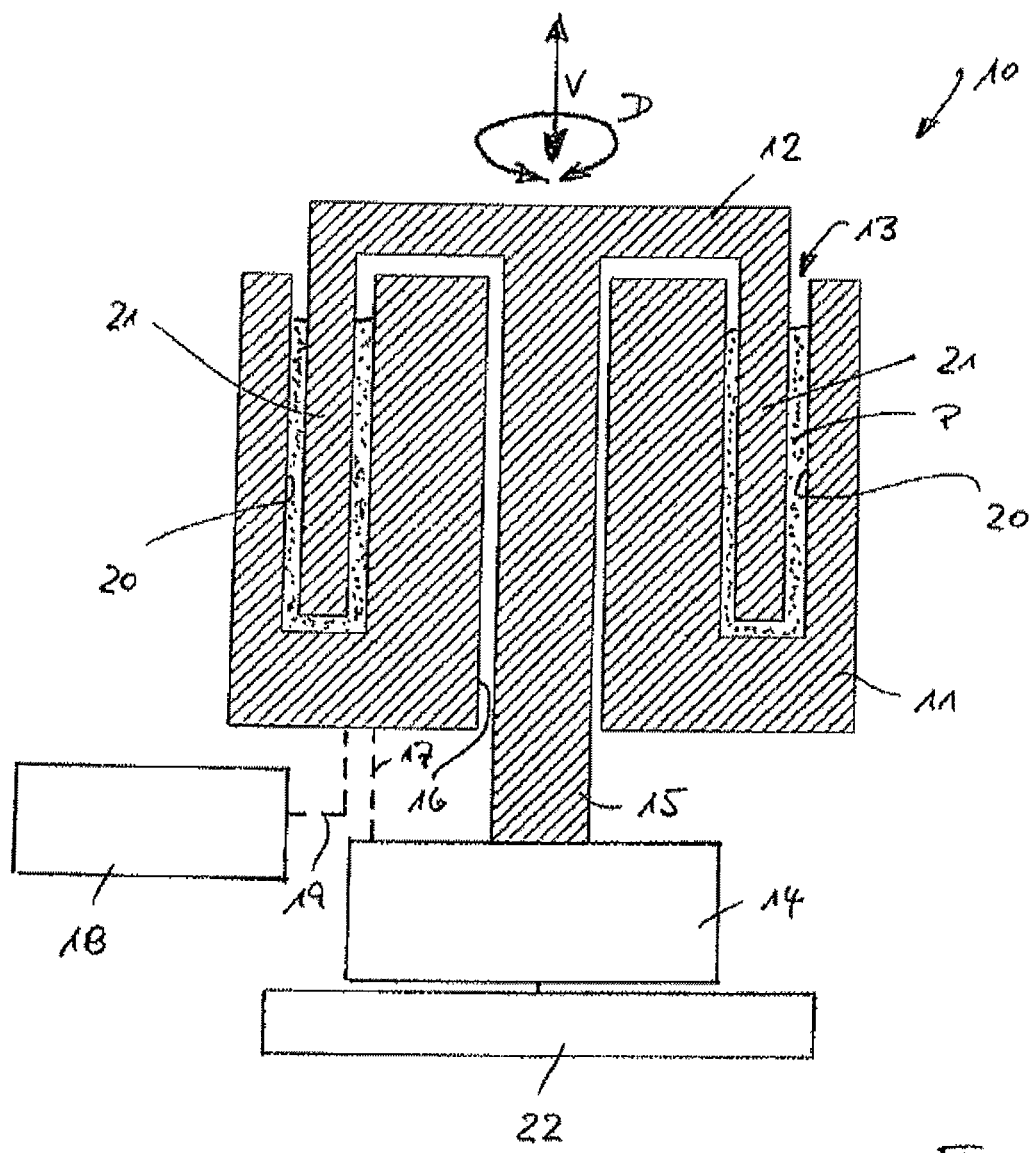

Further details and features of embodiments of the invention are evident from the following description of exemplary embodiments with reference to the drawing, in which:

FIG. 1 shows a schematic representation of a first design (that is, a first embodiment), of the rheometer according to the invention, FIG. 2 shows a schematic representation of an alternative design of the rheometer according to the invention and FIG. 3 shows a schematic representation of a further design of the rheometer according to the invention.

According to FIG. 1, a rheometer (10) has a first, lower measuring part (11), which in the exemplary embodiment represented is in the form of a plate. The first, lower measuring part (11) has a through-bore (16), which extends perpendicularly in relation to the plane of the plate. On the upper side of the first, lower measuring part (11), an upwardly protruding sleeve-shaped attachment (11a) is formed on in the circumferential region of the through-bore (16). Radially outside the sleeve-shaped attachment (11a), an annular groove (11b) surrounding the attachment (11a) is incorporated in the surface of the first, lower measuring part (11).

Arranged under the first, lower measuring part (11) is a drive device (14) in the form of a servomotor, which is connected for example via a releasable coupling to a vertical shaft (15), which penetrates through the first, lower measuring part (15) at the through-bore (16) and on the upper side protrudes beyond the first, lower measuring part (11).

Above the first, lower measuring part (11) and at a distance from it, a second, upper measuring part (12), which in the exemplary embodiment represented is of a conical form, is connected to the shaft (15), the conical surface (12b) facing the first, lower measuring part (11). Formed on the conical surface (12b) is an annular groove (12a), which surrounds the shaft and in which the sleeve-shaped attachment (11a) of the first, lower measuring part (11) engages. The annular groove (12a) and the sleeve-shaped attachment (11a) seal off the through-bore (16). The second, upper measuring part (12) may be connected in a releasable way to the shaft via a coupling (not represented), and consequently be exchanged as and when required.

Between the first, lower measuring part (11) and the second, upper measuring part (12) there is formed a sample space (13), in which an indicated material sample P is arranged. On account of the conical geometry of the second, upper measuring part (12), the sample space (13) has a cross-sectional area that increases radially outward.

The second, upper measuring part (12) can be rotated and/or can be oscillated by means of the drive device (14), as indicated by the double-headed arrow D. In addition, it is possible to lift the second, upper measuring part (12) off from the first, lower measuring part (11) and to lower it onto the latter, as is indicated by the double-headed arrow V.

The first, lower measuring part (11) is usually of a fixed form. Alternatively, however, it is also possible to design the first, lower measuring part such that it can be rotated and/or can be oscillated, it being possible for the drive movement necessary for this either to be taken from the drive device (14), as indicated by a transmission element (17). Alternatively, however, it is also possible to provide the first, lower measuring part with a drive device (18) of its own, the drive movement of which is transferred to the first, lower measuring part (11) via a transmission element (19).

Provided below the drive device (14) is an electronic control and evaluation device (22), which controls or regulates the operating states of the drive device (14) and records and evaluates the measured parameters.

FIG. 2 shows an alternative design of the geometry of the second, upper measuring part (12), and consequently of the sample space (13). The second, upper measuring part (12) is then likewise designed in the form of a plate, so that the sample space (13) has a constant height. The structural design of the exemplary embodiment represented in FIG. 2 otherwise corresponds to the exemplary embodiment according to FIG. 1, to which reference should be made.

FIG. 3 shows a further alternative design of the geometry of the sample space (13). On the upper side of the first, lower measuring part (11) there is formed an annular groove (20), into which the material sample P is filled. The second, upper measuring part (12) is designed in the form of a cup and engages with its vertical flanks (21) in the annular groove (20). The structural design of the exemplary embodiment represented in FIG. 3 otherwise corresponds substantially to the exemplary embodiment according to FIG. 1, to which reference should be made.

The invention claimed is:

1. Rheometer or viscometer with a first measuring part and a second measuring part which form a sample space between them for receiving a material sample, and with a drive device, by means of which at least the second measuring part is able to be rotated and/or oscillated, it being possible for the drive movement of the drive device to be transferred to the second measuring part via a transmission element, characterized in that the drive device is arranged on a side of the first measuring part that is facing away from the second measuring part and that the transmission element penetrates through the first measuring part;

and wherein the first and second measuring parts are configured to retain all the sample between the first measuring part and a side of the second measuring part which is facing the first measuring part.

2. Rheometer or viscometer according to claim 1, characterized in that in the first measuring part there is formed a through-bore, through which the transmission element is led with a close fit.

3. Rheometer or viscometer according to claim 2, characterized in that the transmission element penetrates through the through-bore without a seal.

4. Rheometer or viscometer according to claim 1, characterized in that the transmission element is a shaft.

5. Rheometer or viscometer according to claim 1, characterized in that the drive device is an electric motor.

6. Rheometer or viscometer according to claim 1, characterized in that the first measuring part is of a fixed form.

7. Rheometer or viscometer according to claim 1, characterized in that the first measuring part is able to be rotated and/or oscillated.

8. Rheometer or viscometer according to claim 7, characterized in that the first measuring part and the second measuring part are driven by means of a common drive device.

9. A rheometer or viscometer with a first measuring part and a second measuring part which form a sample space between them for receiving a material sample, and with a drive device, by means of which at least the second measuring part is able to be rotated and/or oscillated, it being possible for the drive movement of the drive device to be transferred to the second measuring part via a transmission element, characterized in that the drive device is arranged on a side of the first measuring part that is facing away from the second measuring part and that the transmission element penetrates through the first measuring part;

wherein the first and second measuring parts are configured to be moved apart and together.

10. A rheometer or viscometer with a first measuring part and a second measuring part which form a sample space between them for receiving a material sample, and with a drive device, by means of which at least the second measuring part is able to be rotated and/or oscillated, it being possible for the drive movement of the drive device to be transferred to the second measuring part via a transmission element, characterized in that the drive device is arranged on a side of the first measuring part that is facing away from the second measuring part and that the transmission element penetrates through the first measuring part;

wherein:
  in the first measuring part there is formed a through-bore, through which the transmission element is led with a close fit;
  the transmission element comprises a shaft;

a sleeve-shaped attachment is formed on the circumferential region of the through-bore in the first measuring part; and an annular groove is formed in the second measuring part which surrounds the shaft and in which the sleeve-shaped attachment of the first measuring part engages.

11. A rheometer or viscometer with a first measuring part and a second measuring part which form a sample space between them for receiving a material sample, and with a drive device, by means of which at least the second measuring part is able to be rotated and/or oscillated, it being possible for the drive movement of the drive device to be transferred to the second measuring part via a transmission element, characterized in that the drive device is arranged on a side of the first measuring part that is facing away from the second measuring part and that the transmission element penetrates through the first measuring part;

wherein:

an annular groove is formed on the first measuring part into which a sample material is able to be filled; and the second measuring part comprises a cup which engages with its flanks in the annular groove.

\* \* \* \* \*

UNITED STATES PATENT AND TRADEMARK OFFICE
CERTIFICATE OF CORRECTION

PATENT NO. : 9,267,871 B2  
APPLICATION NO. : 13/293408  
DATED : February 23, 2016  
INVENTOR(S) : Philippe Sierro Page 1 of 1

It is certified that error appears in the above-identified patent and that said Letters Patent is hereby corrected as shown below:

Claims

Column 4, line 28: In Claim 4, after "element" delete "is" and insert -- comprises --, therefor.

Column 4, line 30: In Claim 5, after "device" delete "is" and insert -- comprises --, therefor.

Signed and Sealed this
Twenty-sixth Day of July, 2016

Michelle K. Lee
*Director of the United States Patent and Trademark Office*